(12) United States Patent
Ark et al.

(10) Patent No.: US 6,257,351 B1
(45) Date of Patent: Jul. 10, 2001

(54) POWERED SURGICAL INSTRUMENT HAVING LOCKING SYSTEMS AND A CLUTCH MECHANISM

(75) Inventors: Timmon Ark; Robert R. Humphris, Jr.; Daniel McCombs, all of Charlottesville, VA (US)

(73) Assignee: MicroAire Surgical Instruments, Inc., Charlottesville, VA (US)

( * ) Notice: Subject to any disclaimer, the term of this patent is extended or adjusted under 35 U.S.C. 154(b) by 0 days.

(21) Appl. No.: 09/342,752

(22) Filed: Jun. 29, 1999

(51) Int. Cl.[7] .................................................. B23Q 5/00
(52) U.S. Cl. .............................. 173/178; 173/29; 173/47; 173/217; 81/474
(58) Field of Search ..................................... 173/178, 176, 173/29, 217, 48, 47, 216; 81/475, 474, 57.11, 469; 188/69

(56) References Cited

U.S. PATENT DOCUMENTS

| | | | | |
|---|---|---|---|---|
| 2,575,903 | * | 11/1951 | Youhouse | 279/52 |
| 2,979,089 | * | 4/1961 | Piesker | 81/57.11 |
| 3,592,087 | * | 7/1971 | Pauley | 173/176 |
| 3,802,518 | * | 4/1974 | Albert | 173/29 |
| 4,448,098 | * | 5/1984 | Totsu | 81/57.11 |
| 4,804,048 | * | 2/1989 | Porth, Jr. | 173/47 |
| 4,823,885 | * | 4/1989 | Okumura | 173/178 |
| 4,878,405 | * | 11/1989 | Wolfe | 81/57.11 |
| 4,986,369 | * | 1/1991 | Fushiya et al. | 173/178 |
| 5,016,501 | * | 5/1991 | Holzer, Jr. | 81/57.11 |
| 5,094,133 | * | 3/1992 | Schreiber | 81/474 |
| 5,251,706 | * | 10/1993 | Evans | 173/29 |
| 5,496,139 | * | 3/1996 | Ghode et al. | 188/69 |
| 5,505,676 | * | 4/1996 | Bookshar | 173/178 |
| 5,664,634 | * | 9/1997 | McCracken | 173/48 |

* cited by examiner

Primary Examiner—Peter Vo
Assistant Examiner—Jim Calve
(74) Attorney, Agent, or Firm—McGuireWoods LLP

(57) ABSTRACT

A surgical instrument having a locking mechanism for preventing an output shaft of the surgical instrument from rotating and a further locking mechanism for mounting a battery pack to a distal end of a housing of the surgical instrument. The surgical instrument further includes a clutch mechanism for limiting the torque of a drive shaft of the surgical instrument. The locking mechanism for preventing the output shaft from rotating includes a locking switch which mates with a locking cap disposed on the output shaft. The locking mechanism for mounting the battery pack to the housing includes a groove at the distal end of the housing and a retaining ring which engages the groove when the battery pack is mounted on the housing. The clutch mechanism includes a clutch plate that interfaces with both the output shaft and the drive shaft and prevents failure of the motor shaft.

19 Claims, 5 Drawing Sheets

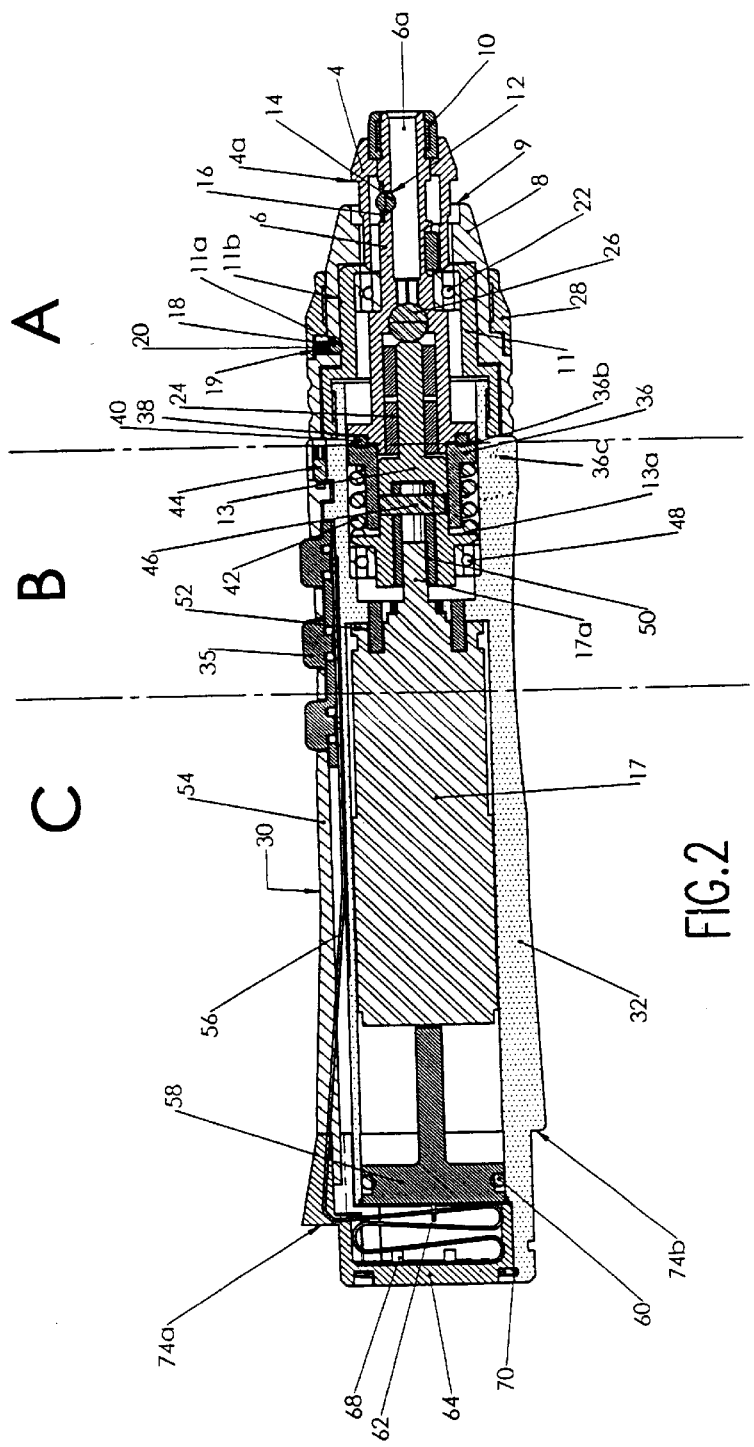
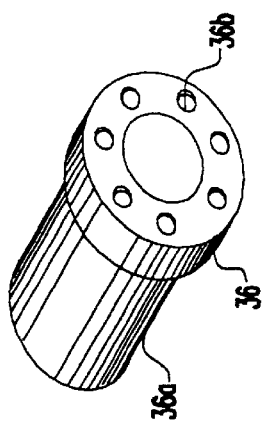
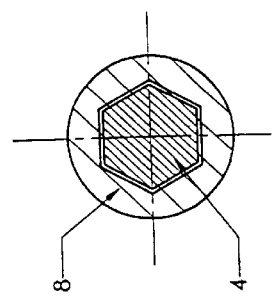
FIG.2B
FIG.2A
FIG.2

POWERED SURGICAL INSTRUMENT HAVING LOCKING SYSTEMS AND A CLUTCH MECHANISM

FIELD OF THE INVENTION

The present invention generally relates to a powered surgical instrument having a locking system and clutch mechanism and, more particularly, to a surgical instrument such as, for example, a screwdriver and the like, having a locking system for locking a power supply thereto and preventing rotation of a drive shaft (and tool), and a clutch mechanism for limiting torque output of the drive mechanism.

BACKGROUND DESCRIPTION

There are countless surgical instruments that are currently used by medical professionals, such as surgeons, dentists, etc. for use in medical procedures, such as, for example, bone fixations and the like. These surgical instruments include, amongst others, saws, drills, screwdrivers and other tools (collectively referred to as "tools"). In many instance, these surgical instruments include battery powered drive mechanisms, or other powered drive mechanisms, in order to drive (e.g., rotate, oscillate, etc.) the surgical tool.

It is well known in the art that these surgical instruments are very complex, yet delicate, instruments which must be used with the utmost care during a surgical procedure. For example, many of these instruments have complex mechanical systems in order to retain the tool within a collet of the surgical instrument such that the tool is firmly retained therein during the surgical procedure. These same tools may also include a mounting and/or locking mechanism in order to hold a battery to the instrument, itself These locking mechanisms can range from simple clamps to more complex key and lock mounts. It is further realized that many of these surgical instruments, especially drills, screwdrivers and the like have adjustable speed controls in order to allow the surgeon or other medical worker to finely adjust the rotational or oscillating speed of the surgical instrument during the surgical procedure.

In accordance with the many procedures that need to be followed during a surgical procedure, it is necessary for the surgeon or other medical personnel to first prepare the surgical instrument prior to the actual surgical event. This initial procedure includes placing a specific required tool into a collet or chuck (collectively referred to as a "collet") of the surgical instrument, as well as ensuring that the battery is fully charged and properly mounted thereon. Thereafter, the surgeon tests the surgical instrument prior to using the same. This latter step includes testing the speed adjustments on the surgical instrument.

It is well known, however, that many of these procedures may be complicated and time consuming. For example, many of the collets currently used include a key and lock mechanism which is both cumbersome to use and time consuming to adjust. Other collet systems are also known, but have other drawbacks associated therewith. For instance, some collet systems are simply threaded collets mechanisms that apply a certain pressure to the tool in order to retain the tool within the surgical instrument. However, these collet systems tend to allow the tool to slip during use thereof, posing a serious danger to both the patient and the surgeon (or other medical worker).

Once the tool is secured within the collet, the powered drive mechanism of the surgical instrument is then activated in order to power the surgical instrument, itself (e.g, drive the tool). It has been found that the use of a powered drive mechanism in surgical instruments during surgery reduces surgeon fatigue and minimizes the amount of time required to perform a particular surgery. However, even though a drive mechanism may assist the surgeon during surgery, there are times during specific surgical procedures that may require the need for a manual surgical instrument. For example, a surgeon may need to apply a large torque to properly place a screw in a bone during a bone fixation procedure, which cannot be performed with a powered tool because the powered surgical instrument is not designed for that particular torque. In this case, it is necessary for the surgeon to change surgical instruments midway through a surgical procedure in order to manually perform the remaining portion of the surgical procedure. This may pose a danger to the patient.

It is further noted that many powered surgical instruments further succumb to other shortcomings, such as failure of the motor shaft. This occurs when the motor shaft is subjected to exceptionally high torque conditions, which is not uncommon during a surgical procedure. Needless to say, the failure of the motor shaft during a surgical procedure is quite dangerous and also renders the surgical instrument useless for future surgical procedures.

Lastly, the surgeon or other medical personnel must also ensure that the power supply (e.g., battery) is properly mounted on the surgical instrument prior to and during use of the surgical instrument. However, with complex mounting systems, such as, key and lock systems, it may be difficult for the surgeon to properly mount the battery onto the housing. This is especially important in the case of battery failure during a surgical procedure such that the surgeon cannot readily and easily remove the failed battery and replace it with a new battery. Also, it is important to ensure that the battery is properly mounted because it has been found that less complicated battery mounting systems do not adequately retain the battery on the housing of the surgical instrument during a surgical procedure. This, of course, poses the problem of a surgical instrument power failure during a surgical procedure which may pose countless dangers to the patient.

Notwithstanding the above discussion, what is needed is a locking system for both the drive mechanism and battery, as well as a clutch mechanism for the drive mechanism. Such a locking system for the battery would be a keyless system and would be easily allow the battery to be mounted and removed from the housing of the surgical instrument. The locking mechanism for the drive mechanism would preferably allow the surgical tool to be used both as a powered and manual tool, whereby in the manual mode the drive mechanism would be prevented from rotating with respect to the motor of the surgical instrument. Moreover, the clutch mechanism would preferably allow a torque of the driving mechanism to be limited such as to prevent failure of a drive shaft of the drive mechanism. These locking and clutch mechanisms would be easy to manufacture and would be robust.

SUMMARY OF THE INVENTION

It is an object of the present invention to provide a surgical instrument that is capable of being used in a manual mode and a powered mode.

It is a further object of the present invention to provide a battery pack mounting system that allows a user to easily mount and remove a battery pack from the housing of a surgical instrument.

It is still a further object of the present invention to provide a mechanism that limits the torque output of a drive shaft of a surgical instrument.

It is still another object of the present invention to provide a mechanism that prevents failure of a motor shaft of a surgical instrument during use thereof In accordance with the objects of the present invention, a surgical instrument having a locking system for mounting a battery pack and preventing rotation of a drive shaft, as well as a clutch mechanism to control the torque of the drive mechanism is provided. The surgical instrument may equally be adapted to be used as a manual or powered screwdriver, drill and the like, and is further designed for intermittent or continuous run time usage.

The surgical instrument of the present invention includes a lock cap that is rotatably mounted to an output shaft and which includes a shaped exterior surface. A lock switch is "fixed" to a housing of the surgical instrument and is capable of axially sliding in a locked position and an unlocked position. The lock switch does not rotate. The lock switch includes a shaped interior surface which substantially corresponds to the shaped exterior surface of the lock cap such that the output shaft is prevented from rotating when the lock switch engages the lock cap. This is the manual mode of the surgical instrument. However, the output shaft is freely rotated via the drive shaft and motor of the surgical instrument of the present invention when the lock switch is in the unlocked position (e.g., disengaged from the lock cap).

The surgical instrument of the present invention further includes a clutch mechanism which prevents failure of the motor shaft. The clutch mechanism includes a clutch plate fixed to the drive shaft and communicating with the output shaft. In the preferred embodiment of the present invention, the clutch plate includes detents that communicate with preferably steel balls (or any other appropriate material) mounted to the output shaft. When a predetermined torque limit is exceeded, the ball bearings "slip" from the detents such that the drive shaft rotates freely with respect to the output shaft. When the predetermined torque limit is not exceeded, the ball bearings are contained within the detents and the drive shaft rotates the output shaft.

A mounting system for a battery pack is also provided. The mounting system includes a groove within the housing of the surgical instrument, and a retaining ring on the battery pack. The retaining ring engages the groove in the mounted position. The retaining ring is controlled by a spring button and is capable of deflecting outward and thereafter returning to its original shape (e.g., elastic deformation).

By using the surgical instrument of the present invention, the drive shaft may be locked so as to use the surgical instrument in a manual mode. This allows the user to have more control of the surgical instrument, such as, for example, to manually insert screws into bones during a bone fixation procedure. The surgical instrument of the present invention further allows the torque output to be limited which protects the motor shaft from exceptionally high torque conditions, and potential failure thereof. Also, the use of a robust and easy to use mounting system for the battery pack allows easy installation and removal of the same.

BRIEF DESCRIPTION OF THE DRAWINGS

The foregoing and other objects, aspects and advantages will be better understood from the following detailed description of a preferred embodiment of the invention with reference to the drawings, in which:

FIG. 2 is sectional view of the surgical instrument of the present invention along line A—A of FIG. 1;

FIG. 2a shows the shaped surface of a lock switch and a lock cap;

FIG. 2b shows a detailed view of a cylindrical collar of a clutch plate;

DETAILED DESCRIPTION OF A PREFERRED EMBODIMENT OF THE INVENTION

The present invention is directed to a surgical instrument having a locking system for mounting a battery pack thereon and for preventing rotation of the drive shaft in a manual mode, as well as a clutch mechanism to control the torque of the drive mechanism. In a preferred embodiment, the surgical instrument is designed for the insertion of small, bone fixation screws, and is applicable to oral, maxillofacial, cranial, spinal and orthopedic procedures. The surgical instrument of the present invention may equally be adapted for use as a manual or powered screwdriver, drill and the like, and is preferably designed for intermittent use (e.g., five seconds of run-time followed by five seconds of inactivity). However, the surgical instrument of the present invention may be used for other run times, and may also be used as a continuous run time surgical instrument. The surgical instrument of the present invention is also adapted for use with a power supply, such as, for example, a battery housed within a battery pack.

In the preferred embodiment, the length of the surgical instrument is less than six inches, and has a maximum outside diameter less than 1.2 inches. In further embodiments, the surgical instrument weighs approximately seven ounces and is made from high-temperature plastics and elastomers, aluminum and stainless steels. The external surfaces are designed so as to be free from lubricant, sealant, nicks, burrs, scratches or other cosmetic defects. The surgical instrument of the present invention preferably includes a torque no greater than approximately 75 oz-in and has various operating speed settings, which include preferably 1. High speed greater than 200 RPM
2. Medium speed greater than 150 RPM
3. Low speed greater than 100 RPM It is understood, however, that the above-specified dimensions of the surgical instrument, including length, width, shape and other variables and quantities may vary. Therefore, numbers and dimensions specified herein are not to be construed as limitations on the scope of the present invention, but are meant to be merely illustrative of one particular application of the present invention.

By using the surgical instrument of the present invention, the drive shaft may be locked (e.g., prevented from rotating with respect to a motor) so that the surgical instrument can be used in a manual mode. This allows the user to have more control of the surgical instrument, such as, for example, to manually insert screws into bones during a bone fixation procedure. The surgical instrument of the present invention further allows the torque output of the drive shaft to be limited which thus protects the motor shaft from exceptionally high torque conditions, and potential failure thereof. Also, the use of a robust and easy to use mounting system for the battery pack allows easy installation and removal of the same.

General Overview of the Surgical Instrument

Figure 1:
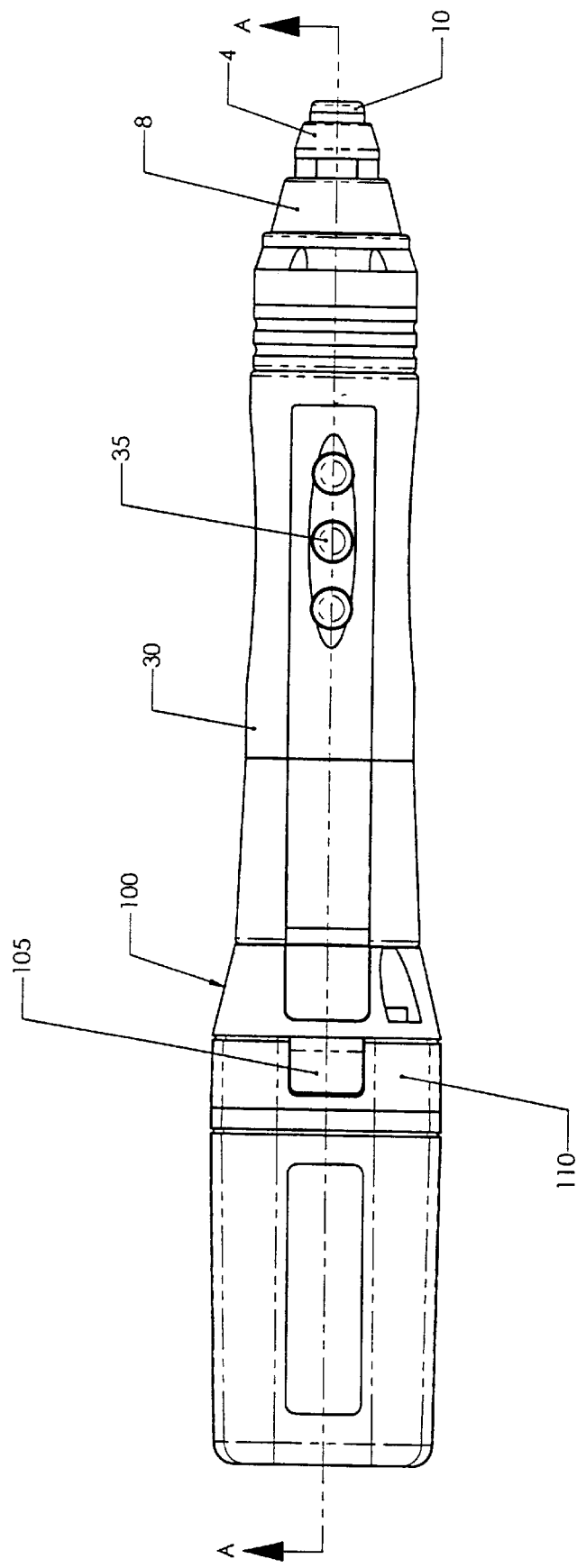
FIG. 1 is a top view of the surgical instrument of the present invention.

Referring now to FIG. 1, a top view of the surgical instrument of the present invention is shown. In general, FIG. 1 shows a surgical instrument 1 having a threaded cap 10 positioned at a proximal end of a housing 30 of the surgical instrument 1. The threaded cap 10 is threaded to an output shaft (not shown) of the surgical instrument, and a lock cap 4 having a substantially hex shaped exterior is retained on the housing 30 via the threaded cap 10. A lock switch 8 is "keyed" to the housing 30 and may interlock with the lock cap 4, as discussed below in detail with reference to FIG. 2.

Still referring to FIG. 1, a plurality of buttons 35 are positioned on the housing 30. These buttons 35 control the various speeds of the tool, e.g., screwdriver, of the surgical instrument 1. At a distal end of the housing 30 is an interface between a battery pack 110 (which houses a battery) and a distal end of the housing 30. The battery pack 110 is mounted to the housing 30 at a battery pack cap 100. The battery pack 110 is removed from the housing 30 by depressing a spring button 105.

Locking Mechanism of Drive Shaft

FIG. 2 shows a sectional view of the surgical instrument of the present invention along line A—A of FIG. 1. FIG. 2 is divided into 3 sections, "A", "B" and "C". Section "A" shows the locking mechanism for preventing the drive shaft from rotating, and will now be discussed in detail.

Specifically, FIG. 2 shows the lock cap 4 rotationally fixed to an output shaft 6 of the surgical instrument 1. The lock cap 4 is further retained axially by the threaded cap 10 which is also fixed to the output shaft 6, preferably by a thread and screw mounting system. It is thus well understood by one of ordinary skill in the art of surgical instruments, that this embodiment of the present invention allows the threaded cap 10 and the lock cap 4 to be rotated with respect to the output shaft 6. The lock cap 4 further includes an exterior surface having a preferably hex shape and a flange 4a. It is well understood by one of ordinary skill in the art that the exterior surface of the lock cap 4 may be square, octagonal or any other well known shape, any one of which is contemplated for use with the present invention.

FIG. 2 further shows a drive housing 11 locked to a handle 32 of the surgical instrument 1. By locking the drive housing 11 to the handle 32, the drive housing 11 is prevented from rotating with respect to the housing 30. FIG. 2 further shows the lock switch 8 slidably mounted to the drive housing 11 thus allowing the lock switch 8 to slide back and forth between a first locked position and a second unlocked position along the axial portion of the drive housing 11. However, by using this arrangement, the lock switch 8, by virtue of being attached to the drive housing 11, is also prevented from rotating. The exterior surface of the drive housing 11 further includes a first lock groove 11a and a second lock groove 11b which provides a means for locking the lock switch 8 in the first locked position and the second unlocked position, as discussed below.

The lock switch 8 is permitted to slide back and forth between the first locked position and the second unlocked position along the axial portion of the drive housing 11 further due, in part, to a clearance 9 between the lock switch 8 and the lock cap 4. Moreover, in embodiments, the lock switch 8 is prevented from sliding beyond the first locked position by the flange 4a of the lock cap 4.

An interior surface of the lock switch 8 at a proximal end thereof is preferably hex shaped and may mate with exterior hex surface of the lock cap 4 when the lock switch 8 is positioned in the first locked position closest to the proximal end of the surgical tool 1. It is well understood by one skilled in the art, that the interior surface of the lock switch 6 may be other shapes such as, for example, square, octagonal or any other well known shape. The only limitation as to the shape of either the lock cap 4 or the lock switch 8 is that they are capable of easily being mated to one another when the lock switch 8 is in the first locked position.

The mating between the lock switch 8 and the lock cap 4 locks the lock cap 4 and thus prevents the output shaft 6 from rotating with respect to a motor 17. As seen in FIG. 2 the output shaft 6 is prevented from rotating by virtue of the lock switch 8 being fixed to the drive housing 11 which, in turn, is prevented from rotating with respect to the housing 30 by virtue of being locked to the handle 32. This allows the surgical instrument 1 to be used in the manual mode. When the lock switch 8 is positioned in the second unlocked position (as shown in FIG. 2), the interior hex surface of the lock switch 8 does not mate with the exterior hex surface of the lock cap 4, thereby allowing the output shaft 6 to freely rotate with respect to a drive shaft 13 (via the motor 17). This allows the surgical instrument 1 of the present invention to be used as a powered surgical instrument.

It is further noted that bores 19 are located within the lock switch 8. Housed within the bores 19 are retention balls 18 and biasing springs 20. A threaded ring 28 is provided about the lock switch 8 to assist in retaining the lock switch 8 on the surgical instrument 1 and to further hold the retention balls 18 and biasing springs 20 within the bores 19 of the lock switch 8.

In the position of the lock switch 8 as shown in FIG. 2 (second unlocked position), the retention balls 18 are biased downward by the springs 20 and engage the first lock groove 11a of the drive housing 11. This provides a means for retaining the lock switch 8 in the second unlocked position thereby allowing the output shaft 6 to freely rotate with respect to the drive shaft 13. In the first locked position of the lock switch 8, the retention balls 18 are biased downward by the springs 20 and engage the second lock groove 11b at another end of the drive housing 11. This provides a means for retaining the lock switch 8 in the first locked position thereby preventing rotation of the output shaft 6. The retention ball and spring mechanism provides the user with a mechanism to assure that the lock switch 8 is properly positioned.

Still referring to section "A" of FIG. 2, the output shaft 6 is provided with a centrally located bore 6a. The centrally located bore 6a houses the surgical tool, such as, for example, a screwdriver or a drill. In embodiments, a retention ball 14 is housed within an aperture 12 having a diameter slightly smaller than the diameter of the retention ball 14. The retention ball 14 extends beyond an interior surface of the centrally located bore 6a due to the configuration (e.g., smaller diameter) of the apertures 12. A retaining spring 16 and preferably a band or material that wraps around the output shaft 6 is partly positioned within a larger diameter of the aperture 12 and provides for proper alignment and biasing of the retention balls 14. In embodiments, a screwdriver having a circumferential groove engages the portion of the retention balls 14 extending beyond the interior surface of the centrally located bore 6a. This mechanism retains the screwdriver within the centrally located bore 6a of the surgical instrument.

Further seen in FIG. 2 are bearings 22 and 24. The bearings 22 are located between the drive housing 11 and the output shaft 6, and the bearings 24 are located between the drive shaft 13 and the output shaft 6. The bearings 22 and 24 allow the components of the surgical instrument 1 to rotate freely with respect to one another. Additionally, at least bearings 24 balance the loading between the output shaft 6 and the drive shaft 13. Any known bearings of any suitable type may be used with the surgical instrument of the present invention. Moreover, at a proximal end of the drive shaft is a ball 26. The ball 26 transmits thrust to the drive shaft 13, as well as providing a means for transmitting a load from the tool to the remaining components, such as a back bearing, of the surgical instrument 1.

FIG. 2a shows the shaped surface of the lock switch 8 and the lock cap 6 in the lock (e.g., engages) position. FIG. 2a shows a hex shape of the lock switch 8 and the lock cap 6; however, as discussed above, shapes such as, for example, square, octagonal or any other well known shape are contemplated for use with the present invention.

Clutch Mechanism

FIG. 2 further shows the clutch mechanism of the present invention. The clutch mechanism of the present invention preferably limits the torque output to approximately 75 oz-in, but may equally be adjusted to other tolerances depending on the particular use of the present invention. It is noted, however, that the clutch mechanism of the present invention is preferably designed to slip at 75 oz-in so as to not exceed the failure torque of the motor shaft 17a while still being sufficient for screw insertion. The clutch mechanism may also prevent the tool from stripping the screw or other causing other damage to the screw during a bone fixation procedure when the torque exceeds a certain limit. Thus, the clutch mechanism of the present invention provides at least two advantages, including:

1. Protecting the drive shaft from exceptionally high torque conditions.
2. Providing an upper limit to the amount of torque that the surgical instrument of the present invention can produce when powered by a battery.

Referring to section "B" of FIG. 2, the clutch mechanism of the present invention comprises two independent shafts, the drive shaft 13 and the output shaft 6 connected by a spring-loaded clutch plate 36. The clutch plate 36, drive shaft 13, and motor 17 are connected so that they rotate in unison.

In the clutch mechanism of the present invention, the output shaft 6 contains a plurality of apertures 38 which hold a plurality of clutch balls 40. In addition, the clutch plate 36 includes a plurality of detents 36b which contain the plurality of clutch balls 40 therein during normal power operation of the surgical instrument 1. In the preferred embodiment, there are more detents 36b than clutch balls 40, and the clutch balls 40 may be made from any appropriate material such as steel. A coil spring 42 is wound about a cylindrical collar 36a of the clutch plate 36 and is biased against a collar 13a of the drive shaft 13. (See FIG. 2b for a detailed view of the cylindrical collar 36a of the clutch plate 36.) The biasing force of the coil spring 42 holds the clutch plate 36 in contact with the output shaft 6.

In operation, when the torque of the drive shaft is within a predetermined limit (e.g., 75 oz-in), the clutch balls 40 are contained within the detents 36b on the clutch plate 36 and the output shaft 6 rotates with the clutch plate 36, drive shaft 13 and motor 17 (and motor shaft 17a). When the torque limit is exceeded, the clutch balls 40 on the output shaft 6 are not contained within (e.g., slip out) the detents 36b and the output shaft 6 does not rotate with the motor 17. That is, the torque applied on the motor shaft 17a overcomes the biasing force of the coil spring 42 such that the biasing force of the coil spring 42 cannot contain the clutch balls 40 within the detents 36b. This provides for a fail safe system in which failure of the motor shaft 17a is prevented when a predetermined torque limit is exceeded by the motor 17 and/or drive shaft 13.

Still referring to section "B" of FIG. 2, a pin 42 is provided between a motor coupler 50 and the output shaft 6. This enables the drive shaft 13 to be powered (e.g., rotated) by the motor 17. A bearing 48 is also placed between the drive shaft 13 and the housing 30 in order to distribute the load between the output shaft 6 and the housing 48, and to further allow the drive shaft 13 to freely rotate. Also, positioning pins 52 are positioned between the motor 17 and the housing 30 in order to properly position the motor 17 within the housing as well as to prevent the motor 17 from rotating during use thereof These features are not considered critical to the understanding of the clutch mechanism of the present invention, and are provided herein to simply show further features of the surgical instrument.

Motor Compartment and Connection and Sealing Portion of Surgical Instrument

FIG. 2 further shows a rear portion of the surgical instrument 1 of the present invention. More specifically, section "C" of FIG. 2 shows the motor 17 mounted within the housing 30. The housing 30 includes a handle 32 and a button cover 54 for covering the power buttons 35. A flexible circuit 56 is provided between the buttons 54 and a battery contact 68. A plug 58 is positioned within the housing 30 and retains the motor 17 therein. An o-ring 60, of any suitable material, is positioned about the plug 58 so as to seal the motor 17 within the housing 30. The o-ring 60 protects the motor 17 during cleaning and/or sterilization of the surgical instrument 1.

Figure 6:
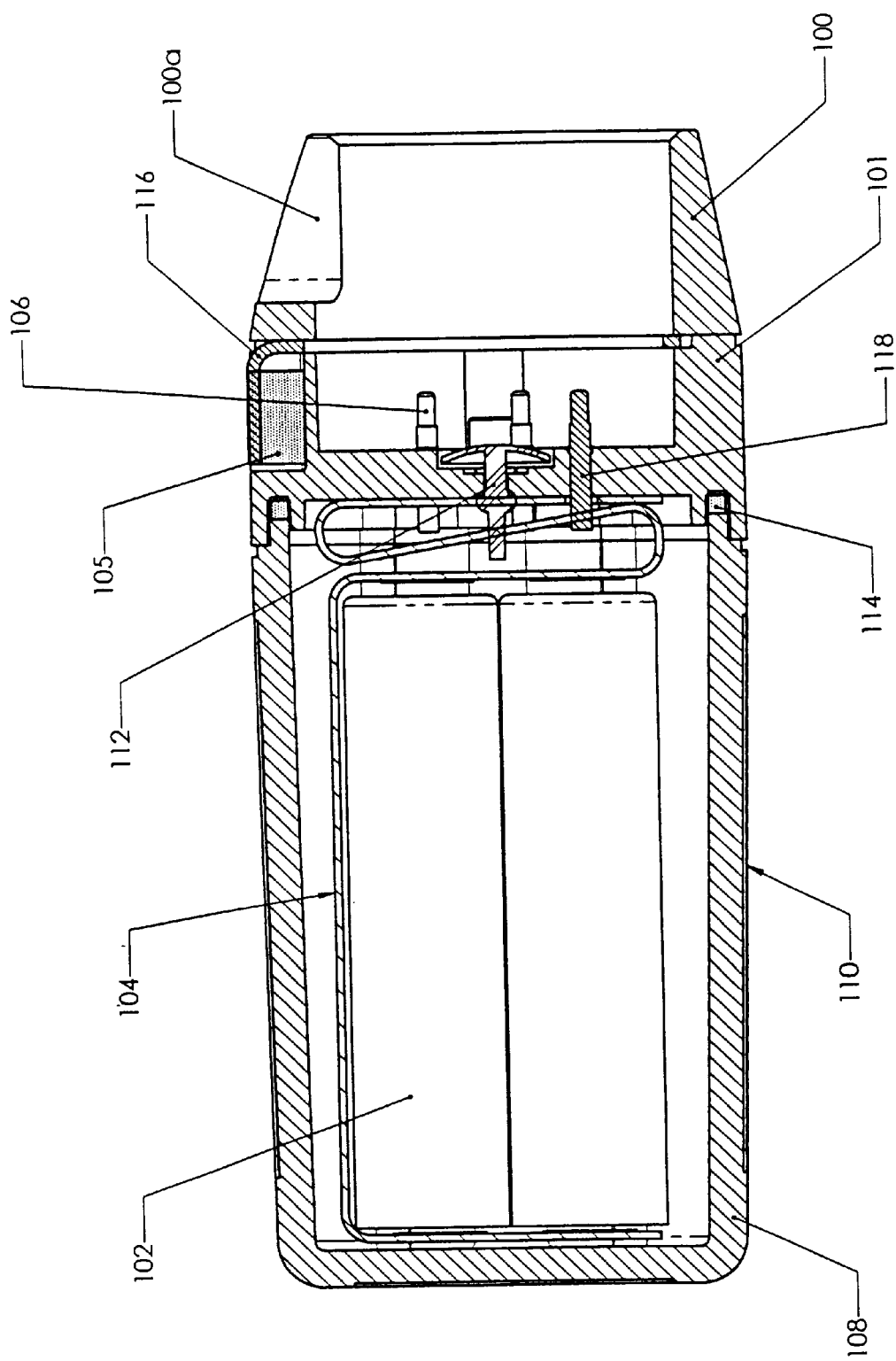
FIG. 6 is sectional view of the battery pack of the present invention along line B—B of FIG. 4.

Two motor contacts 62 extend from the plug 58 and provide a contact between the motor 17 and a battery 102 (FIG. 6). An end shell 64 having apertures 64a aligned with the battery contacts 68 are provided at a distal end of the housing 30. A retaining ring 70 holds the end shell 64 to the housing 30. The end shell 34 includes a lip 74a and the housing 30 includes a lip 74b, both which prevent the battery pack 110 from extending past a predetermined location on the housing 30. Lastly, a groove 72 is positioned at the distal end of the housing 30 and is used as a retaining groove to retain the battery pack 110 thereon (as discussed below).

Battery Pack

Figure 3:
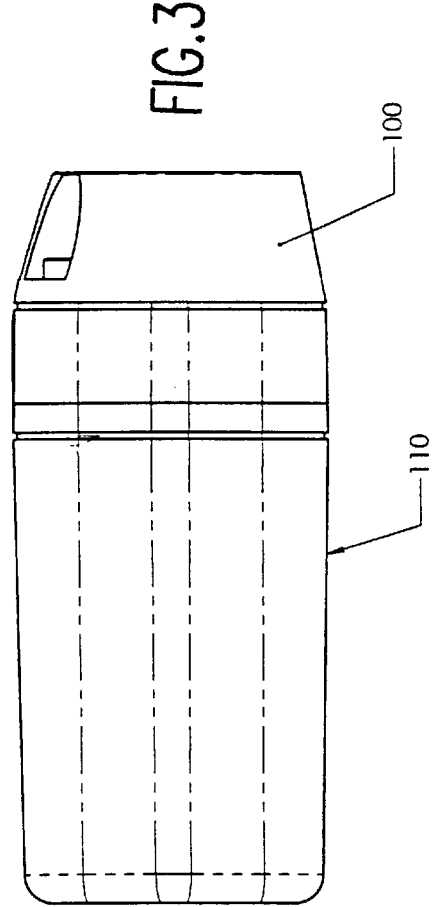
FIG. 3 is a side view of the battery pack of the present invention.

FIG. 3 shows a side view of the battery pack of the present invention. More specifically, FIG. 3 shows the pack cap 100 and the battery casing 110. The pack cap 100 interfaces and is mounted over the end shell 64 of the surgical instrument (discussed with reference to FIG. 7).

Figure 4:
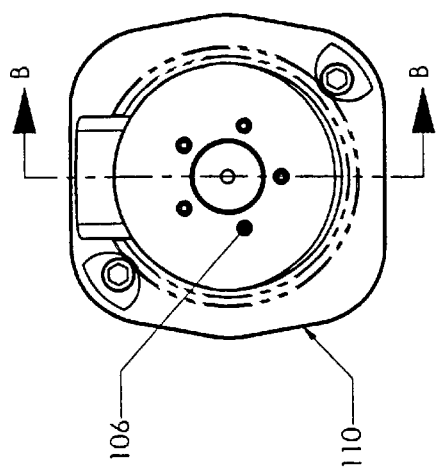
FIG. 4 is a front view of the battery pack of the present invention.

FIG. 4 shows a front view of the battery pack, and more specifically shows contact pins 106. The contact pins 106 are inserted into the apertures 64a in order to contact the battery contacts 68. In preferred embodiments, the contacts 106 do not extend past the pack cap 100, which is shaped as a collar.

Figure 5:
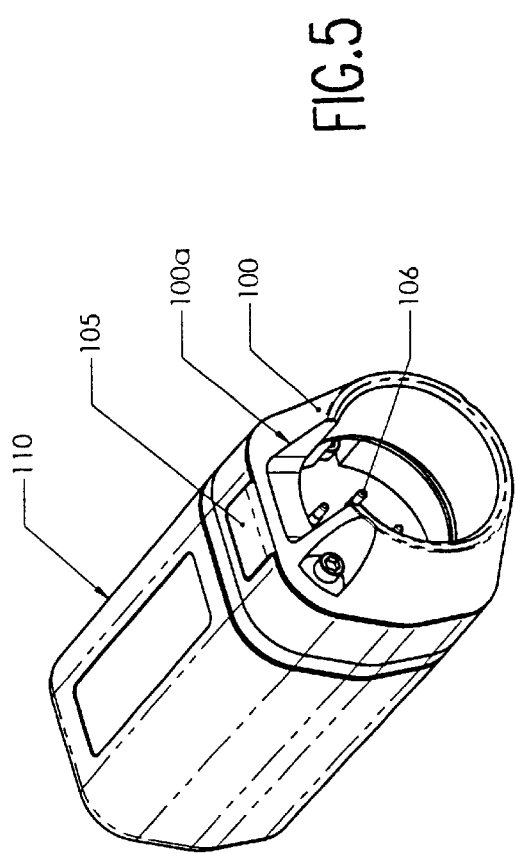
FIG. 5 is an isometric view of the battery pack of the present invention.

FIG. 5 is an isometric view of the battery pack of the present invention and shows more clearly a recess 100a in the battery cap 100. When the battery pack 110 is mounted on the housing 30, the recess 100a contacts the lip 74a of the end shell 64 and the remaining portions of the battery cap 100 contact the lip 74b of the housing. This prevents the battery pack 110 from being extended past a predetermined location on the housing 30.

FIG. 6 is a sectional view of the battery pack of the present invention along line B—B of FIG. 4. As seen clearly from FIG. 6, the battery pack 110 includes the battery pack cap 100, a middle portion 101 and a battery case 108. A battery pack seal (e.g., o-ring) 114 seals the battery case 108 to the middle portion 101.

Still referring to FIG. 6, the battery case 108 houses the battery 102 therein, and a flexible circuit 104 within the battery case 108 extends from the battery 102 to the contacts 106. In turn, the contacts 106 extend into the middle portion 101 of the battery pack 110. The battery contacts 106 are preferably metallic, gold plated and complete the circuit between the motor 17 and the battery 102. A probe 118, preferably a metallic material, is spring loaded and provides a means for interfacing between the battery 102 and a battery charger (not shown). The battery interface probe 118 is retracted when the battery pack 110 is mounted on the housing 30.

FIG. 6 further shows an umbrella valve 112 extending between the middle portion 101 and the battery case 108 of the battery pack 110. The umbrella valve 112 is a one way valve which allows gases to escape from the battery case 108, while preventing water or other fluids to enter the battery case 108. The umbrella valve 112 is especially useful when sterilizing the battery pack 110. That is, the umbrella valve 112 prevents sterilization fluids from entering the battery case 108 thus potentially destroying the battery 102, while allowing gases that build up during the sterilization process to escape from the battery case 108.

Battery Mounting System

FIG. 6 further shows the spring button 105 and a retaining ring 116 (preferably elastic) used to mount the battery pack 110 to the housing 30 of the surgical instrument. In general, in order to mount the battery pack 110 to the distal end of the housing 30, the spring button 105 is depressed which, in turn, deflects the retaining ring 116 outwardly. The battery cap 110 is then mounted onto the housing and the spring button 105 is released. At this time, the contact 106 of the battery 102 is in contact with the battery contact 68 of the housing 30. The battery pack may also be mounted to the distal end of the housing 30 by simply sliding the battery cap 100 over the distal end of the housing 30 and allowing the retaining ring 106 to engage the groove, without depressing the spring button 105.

When the spring button 105 is released, the retaining ring 116 deflects to its original position and engages the groove 72 at the distal end of the housing 30. In this position, the recess 100a contacts the lip 74a of the end shell 64 and the remaining portions of the battery cap 100 contact the lip 74b of the housing 30. In order to disengage the battery pack 110 from the housing, the reverse steps are performed.

Figure 7:
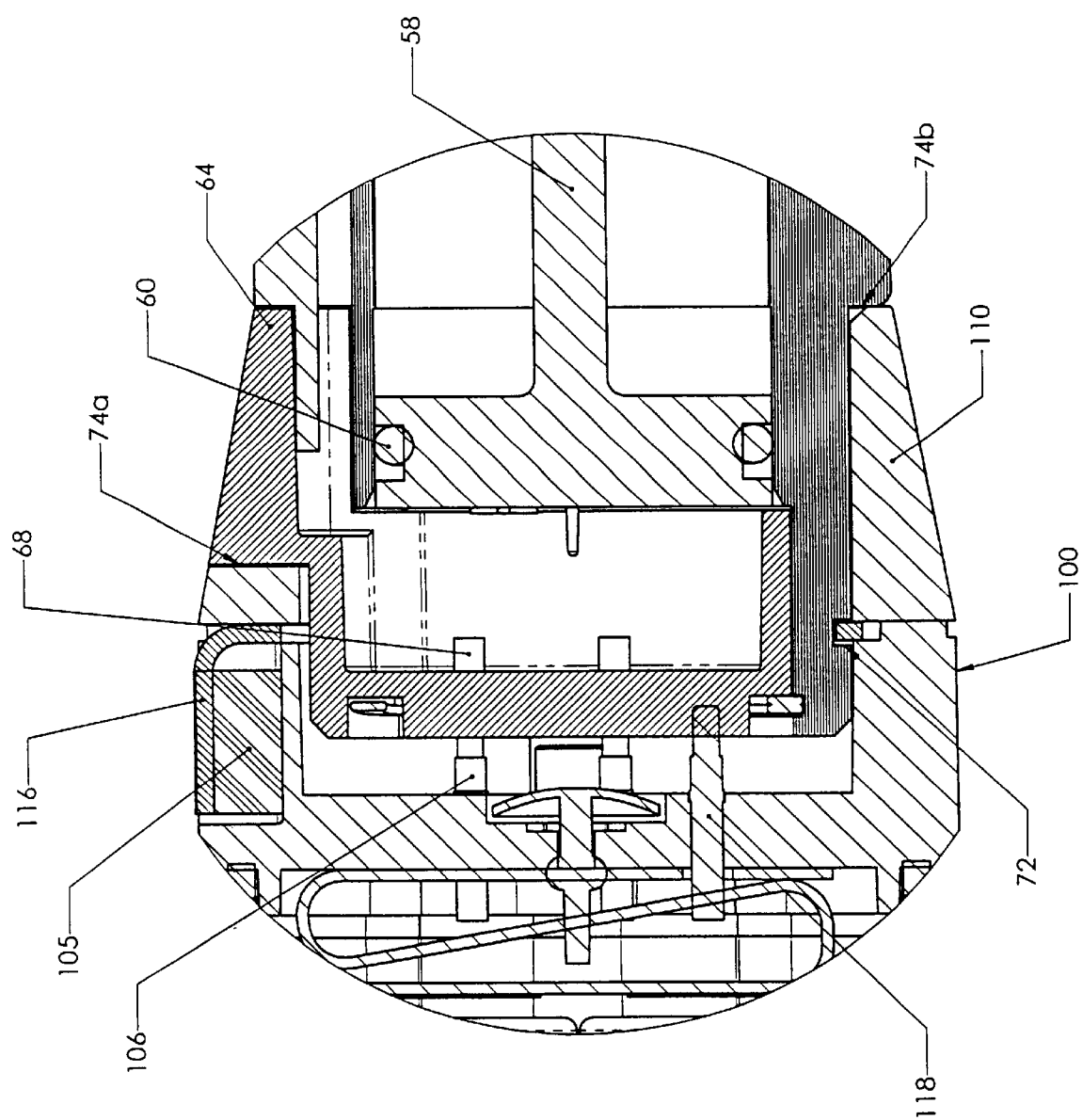
FIG. 7 is an exploded view of a connection between the battery pack and the surgical instrument of the present invention.

FIG. 7 shows an exploded view of a connection between the battery pack and the surgical instrument of the present invention. Specifically, the retaining ring 116 is engaged with the groove 72, and the recess 100a contacts the lip 74a of the end shell 64 and the remaining portions of the battery cap 100 contact the lip 74b of the housing 30. Moreover, the contacts 106 are connecting to the battery contacts 68 thereby providing the required energy to power the motor 17.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A surgical instrument, comprising;
    means for preventing rotation of an output shaft, said preventing means being housed within a housing of the surgical instrument, said rotation preventing means including a locking switch slidable between a first position and a second position, said locking switch being lockable in said first portion and said second position by biasing a ball engaging with a first groove and a second groove of a drive housing associated with said housing, respectively, said ball being biased by a spring and said locking switch being non-rotatable;
    means for preventing failure of a motor shaft, said motor shaft driving said output shaft, said failure preventing means including:
        apertures positioned on said output shaft for holding contacting balls,
        a clutch plate having a plurality of detents, said contacting balls being contained substantially within said detents when a torque on said drive shaft is within a predetermined limit, said contacting balls disengaging from said detents and remaining within said apertures when said torque exceeds said predetermined limit; and
    means for mounting a battery pack to said housing, said mounting means including a retaining spring communicating with a groove of said housing.

2. The surgical instrument of claim 1, wherein said rotation preventing means further includes:
    a locking cap rotationally fixed to said output shaft;
    said locking switch including an interior surface of said locking switch being shaped to engage with an exterior surface of said locking cap, said locking switch and said output shaft being prevented from rotating when said locking cap and said locking switch engage with one another.

3. The surgical instrument of claim 2, wherein said interior surface of said locking switch and said exterior surface of said locking cap are substantially a same shape.

4. The surgical instrument of claim 2, wherein:
    said locking switch is slidable between said first position which is a first locked position and said second position which is a second unlocked position,
    said locking switch and said locking cap engage with one another when said locking switch is in said first locked position, thereby preventing rotation of said output shaft.

5. The surgical instrument of claim 1, further comprising a retaining ring, said retaining ring holding said spring within a bore of said locking switch.

6. The surgical instrument of claim 1, wherein said failure preventing means is capable of preventing a tool from stripping a screw or otherwise causing other damage to the screw during a surgical procedure.

7. The surgical instrument of claim 1, wherein said clutch plate includes a collar substantially surrounding said motor shaft.

8. The surgical instrument of claim 7, further comprising a spring positioned about said collar, said spring being biased towards said output shaft thereby holding said clutch plate in contact with said output shaft.

9. The surgical instrument of claim 1, wherein said mounting means includes contact means for contacting an electrical contact with a battery contact.

10. The surgical instrument of claim 1, wherein said mounting means includes at least one lip about said housing of said surgical instrument, said lip preventing said battery pack from extending past a predetermined location on said housing.

11. A surgical instrument having a locking mechanism for preventing rotation of an output shaft of said surgical instrument, said surgical instrument comprising:
- a lock cap having a shaped exterior surface, said lock cap being fixed to said output shaft;
- means for preventing rotation of said lock cap and said output shaft when said preventing means is in a first locked position, said rotation preventing means including a locking switch having an interior surface, the exterior surface of said lock cap and the interior surface of said locking switch being substantially a same shape such that the interior surface of the locking switch and the exterior surface of said locking cap engage with one another in the first locked position to prevent rotation of said output shaft;
- a drive housing fixed to a housing of said surgical instrument, said locking switch locking in a first position and a second position on said drive housing and is further axially slidable on said drive housing between said first position and said second position and is non-rotatable; and
- retaining means for retaining said locking switch in said first and said second position, said retaining means including:
  - a first groove and a second groove in said drive housing; and
  - a spring biasing means positioned with respect to said locking switch, said spring biasing means including a spring which biases a ball in engagement with said first groove in said first position and said second groove in said second position.

12. The surgical instrument of claim 11, further comprising a retaining ring, said retaining ring holding said spring biased means within a bore of said lock switch.

13. A surgical instrument having a clutch mechanism for limiting a torque on a motor shaft of said surgical instrument, said surgical instrument comprising:
- a clutch plate having a plurality of detents;
- a drive shaft contacting said clutch plate;
- an output shaft having apertures for holding contacting balls, said output shaft being located proximate to said drive shaft and said contacting balls being contained within said detents when a torque on said drive shaft is within a predetermined limit, said contacting balls disengaging from said detents and remaining within said apertures when said torque exceeds said predetermined limit;
- means for preventing rotation of said output shaft, said rotation preventing means being housed within a housing of the surgical instrument, said rotation preventing means including a locking switch slidable between a first position and a second position;
- a drive housing fixed to said housing, said locking switch locking in said first position and said second position on said drive housing and axially slidable on said drive housing and being non-rotatable;
- retaining means for retaining said locking switch in said first and said second position, said retaining means including:
  - a first groove and a second groove in said drive housing; and
  - a spring biasing means positioned with respect to said locking switch, said spring biasing means including a spring which biases a ball in engagement with said first groove in said first position and said second groove in said second position.

14. The surgical instrument of claim 13, wherein said clutch plate includes a collar substantially surrounding said drive shaft.

15. The surgical instrument of claim 14, further comprising a spring positioned about said collar, said spring being biased toward said output shaft thereby holding said clutch plate in contact with said output shaft.

16. The surgical instrument of claim 13, wherein said predetermined limit of said torque is approximately 75 oz-in.

17. The surgical instrument of claim 13, wherein said detents form a smaller depression in said clutch plate than a depression of said apertures formed in said output shaft such that said contacting balls are seated further in said apertures than said detents.

18. The surgical instrument of claim 13, wherein said drive shaft is coupled to a motor of said surgical instrument, said motor rotates said drive shaft and said output shaft.

19. The surgical instrument of claim 13, wherein said clutch mechanism prevents one of a failure of the motor shaft and further prevents a tool from stripping a screw or causing other dangerous to the screw during a surgical procedure.

* * * * *